United States Patent [19]

Garrett et al.

[11] 4,181,245
[45] Jan. 1, 1980

[54] CASETTE FOR USE WITH AN I.V. INFUSION CONTROLLER

[75] Inventors: Scott T. Garrett, Highland Park; Lee K. Kulle, Mundelein; William L. Rudzena, McHenry, all of Ill.

[73] Assignee: Baxter Travenol Laboratories, Inc., Deerfield, Ill.

[21] Appl. No.: 878,966

[22] Filed: Feb. 17, 1978

[51] Int. Cl.² .............................................. A61M 5/14
[52] U.S. Cl. .............................. 222/450; 128/214 R; 251/61.1; 251/331
[58] Field of Search ............ 128/214 R, 214 C, 214.2, 128/227; 251/61.1, 331; 222/207, 212, 214, 447, 450, 451, 452, 440, 445, 449, 206

[56] References Cited

U.S. PATENT DOCUMENTS

| | | | |
|---|---|---|---|
| 1,889,663 | 11/1932 | Ilyus | 222/447 UX |
| 2,895,653 | 7/1959 | Giepen | 222/452 |
| 2,903,165 | 9/1959 | Hanson et al. | 222/447 |
| 4,121,584 | 10/1978 | Turner et al. | 222/450 X |

FOREIGN PATENT DOCUMENTS

1203145 1/1960 France.

Primary Examiner—David A. Scherbel
Attorney, Agent, or Firm—Paul C. Flattery; John P. Kirby, Jr.; Garrettson Ellis

[57] ABSTRACT

A casette employing a stretchable elastomeric membrane used with an intravenous infusion controller to limit the field flow to a patient. The casette includes two sections of rigid plastic fused together with the membrane between them. The membrane and one section of the plastic form the channel through which the intravenous solution passes. The other section of plastic limits the expansion of the membrane to a predetermined size in order to provide the casette with a chamber of known volume. A valving configuration in the inlet and outlet to the chamber controls the fluid flowing through the casette and, thus, to the patient. Each valve includes a section of the elastomeric membrane in proximity to a configured portion of the piece of plastic forming the channel with the membrane. To close the valve, the controller extends a shaped elongated member through the other section of plastic to stretch the membrane and force it into contact with the configured plastic. Alternately opening and closing the inlet and the outlet ports at appropriate time intervals limit the fluid that can pass through the casette. The plastic forming the chamber with the membrane may also include a groove to allow the passage of fluid through the casette when outside the controller. Small circular grooves allow for the removal of air bubbles in the chamber when first priming it for use with the intravenous solution.

23 Claims, 12 Drawing Figures

CASETTE FOR USE WITH AN I.V. INFUSION CONTROLLER

CROSS-REFERENCES TO RELATED APPLICATIONS

The controller discussed in the subject application may make use of the Z-shaped bracket shown in the design patent application of Nick Zissimopoulous entitled "CASETTE HOLDER AND TRANSPORTER IN A FLUID FLOW LIMITING DEVICE", U.S. application Ser. No. 878,965, filed Feb. 17, 1978, now abandoned. It may also utilize the mechanical components disclosed in the pending patent application "IMPROVED FLUID-FLOW LIMITING APPARATUS FOR USE WITH INTRAVENOUS SOLUTION ADMINISTERING EQUIPMENT" of Nick Zissimopoulous, application Ser. No. 878,970, filed Feb. 17, 1978; the electronic circuitry of the pending patent application "DIGITAL ELECTRONICS AND CASETTE SIZE FOR INTRAVENOUS FLUID-FLOW LIMITING EQUIPMENT" of Vincent L. Knigge and Norman Shim, Ser. No. 878,846, filed Feb. 17, 1978; the electromagnetic device of the pending patent application "LOW CURRENT E-FRAME ELECTROMAGNET WITH A PERMANENT MAGNET ARMATURE FOR AN I.V. VALVING CONTROLLER" of Orest Hrynewycz, U.S. application Ser. No. 878,650, filed Feb. 17, 1978; and either of the electromagnet shapes displayed in the design patent applications "E-FRAME ELECTROMAGNET HAVING A PERMANENT MAGNET ROCKER-ARM ARMATURE" of Orest Hrynewycz, U.S. application Ser. No. 878,649, filed Feb. 17, 1978, and now abandoned; and "E-FRAME ELECTROMAGNET HAVING PERMANENT MAGNETS ATTACHED TO A ROCKER-ARM ARMATURE" of Nick Zissimopoulous, application Ser. No. 878,832, filed Feb. 17, 1978 and now abandoned. In addition to aspects of the above applications, the casette in the subject application may utilize a structure including the valving configurations of the pending patent application "NON-CRITICALLY ALIGNED VALVING DEVICES FOR FLOW RATE LIMITING CASETTE USED IN INTRAVENOUS SOLUTION ADMINISTERING/EQUIPMENT" of Scott T. Garrett, Thurman S. Jess, Vincent L. Knigge, Lee K. Kulle, William L. Rudzena and Nick Zissimopoulous, U.S. application Ser. No. 878,847 filed Feb. 17, 1978; and the shape shown in the design patent application "VALVABLE CASETTE" of Lee K. Kulle and William L. Rudzena, Ser. No. 878,962, filed Feb. 17, 1978 and now abandoned. All of these referenced applications have the same filing date as the subject application.

In the administration of intravenous fluids to a patient, controlling the flow rate of the liquid assumes a critical importance. A patient can suffer serious and deleterious consequences should the amount of liquid he receives in a particular period of time exceed a safe limit.

The seriousness of an excessive flow rate readily appears where the intravenous solution contains medication. The tissues of the arterial system and those surrounding it can become traumatized by a concentrated dose of medicant. Accordingly, the flow rate of the medication-containing solution must remain under strict control to avoid injuring the recipient.

However, an excessively large concentration of isotonic solution containing nothing other than the usual nutrients such as glucose can also effect serious damage upon a person. The tissues around the body require the continued receipt of the various components of blood in approximately normal concentration to continue their vital biochemical processes. Thus, the administering apparatus for even oridinary, unmedicated intravenous solutions must carefully control the rate of its administration.

Until recent times, the device for limiting the rate of flow of a solution to a patient consisted of some form of clamping device. This type of device limits the cross-sectional area of the flexible tube carrying the solution from the bottle to the patient. The attendant adjusts the clamping device until the rate of flow, measured by the frequency of drops in a drip chamber falls within appropriate limits.

Nonetheless, these flow-restricting clamps do not always prevent an excessive flow rate. First, the clamps have not proven themselves infallible against unintended and undesired changes in their adjustment. Thus, the device may undergo an unnoticed change of adjustment and allow a dangerously large amount of solution to pass to the patient.

The hose clamp also suffers from a more subtle problem. The flow rate depends upon the difference in height between the top of the liquid in the bottle and the patient's arm. Increasing that distance provides a greater hydrostatic pressure and increases the rate. Usually, the attendant initially adjusts the clamping device to provide the desired flow rate and then leaves to perform his other responsibilities. Subsequent to his departure, the patient may move about and actually lower his arm and increase the distance between it and the bottle of solution. This movement increases the hydrostatic pressure and thus results in a larger flow rate than initially established by the attendant.

Furthermore, the patient may become somewhat nervous while the attendant works upon him. This could particularly represent the situation during the initial insertion of the hypodermic needle into his vein. This nervousness results in an increase of his internal blood pressure. This heightened blood pressure reduces the pressure differential established by the height of the I.V. solution above his arm. After the initial adjustment by the attendant and his departure from the room, the patient may become calmer and undergo a concomitant decrease in his blood pressure. As a result, the pressure differential propelling the fluid to the patient increases and thus provides a higher, and perhaps dangerous, flow rate.

To prevent the injuring of a patient by a procedure intended to benefit him, various instruments have recently provided positive control over the flow rate of the intravenous solution. An important example of this type of instrument has taken the form of a peristaltic pump operating on the flexible tubing extended between the bottle of I.V. solution and the patient. The pump operates only upon the outside of the tubing and, thus, poses substantially no risk of introducing foreign substances in the I.V. liquid. Moreover, the pump actually performs a dual function. Its pumping action first assures the continued flow of solution regardless of the absence or presence of a hydrostatic pressure of any magnitude. Secondly, of course, its peristaltic action only permits a predetermined amount of fluid to reach the patient. It thus guards against a dangerously large concentration of the foreign I.V. solution within the patient's blood stream.

The peristaltic pumping machines have achieved their prime objectives. They limit the total flow rate of solution to the patient; maintain a desired flow; and pose no danger to the required sterility. However, they possess attributes which reduces their desirability of specific circumstances.

The peristaltic pump operates by squeezing the flexible I.V. tubing at a number of points and moving those points in the direction of the patient. Between these points, the tubing must substantially resume its prior shape to allow a volume of fluid to move between the contracted points. This procedure occurs over a very short length of the tubing and occurs a vast multitude of times during the administration of the solution. For a patient on continuous intravenous therapy, the same tubing may remain in place and in use for up to 24 hours.

Tubing used in intravenous sets does not, however, possess absolute flexibility and resiliency. After a period, the action of the peristaltic pump can actually cause the tubing in the active region to collapse and blockage the further flow of fluid. Using a different type of tubing does not necessarily solve this problem. The tubing must meet stringent requirements such as not leaching any detectable amount of plastisizing solvent into the I.V. solution. Thus, tubing of high quality for intravenous fluid may not possess the capability of withstanding the constant force administered by the pump.

Furthermore, the peristaltic pump, with its motor and controls, constitutes a relatively heavy piece of equipment. Accordingly, it must have a surface upon which to rest during the time it finds use in administering intravenous fluids. Finding such a surface adjacent to a patient's bed, for example, may pose a serious inconvenience. It may, moreover, represent an impossibility for a patient not in a controlled environment; those moving between rooms in a hospital or receiving therapy at the scene of an accident may be denied the benefits of this type of apparatus.

Furthermore, the motor of the peristaltic pump consumes substantial electricity. It, thus, generally requires connection to the usual electric outlet with its constant supply of electric energy.

Connecting a piece of equipment intended for use with an I.V. administering set to an electrical outlet imposes further limitations and requirements upon the piece of apparatus. It necessitates the inclusion of protective components to assure that no unsafe electrical potentials can endanger the patient or even the attendant. Moreover, the apparatus can only find use near such an electrical outlet, thus limiting its range of applications.

An alternative to the peristaltic pump appears in R. Scott Turner et al.'s U.S. patent application Ser. No. 732,946. There they provide a combination of a casette and a controller for keeping the flow rate of the I.V. solution at or below a preset value. Turner et al.'s apparatus does not attempt to provide any motive force to impel the fluid into the patient; it relies upon gravity for that. Thus, it prevents the flow rate from exceeding a level considered safe for the patient.

The casette component of Turner et al.'s apparatus becomes part of the flow path for the fluid to the patient. It includes a metering chamber having a predetermined maximum volume through which the fluid must flow on its journey to the recipient. The casette includes two sections of rigid plastic with a section of resilient plastic material, such as polyurethene, sandwiched between them. The fluid, flowing through the casette, contacts the resilient material and only one section of the rigid plastic.

The resilient plastic, forming part of the metering chamber of predetermined volume, flexes between two configurations. In one, the chamber has substantially no volume. In the other, the chamber expands to the predetermined volume. The second piece of rigid plastic keeps the resilient polyurethene from assuming a configuration that would result in an excessively large volume for the metering chamber.

The casette also provides an inlet and an outlet to the chamber. Each opening includes a valving device. The controller functions primarily in controlling the valves to limit the amount of fluid flowing through the casette. In particular, the controller opens the inlet, allows the metering chamber to fill, and then closes the inlet. Subsequently, the outlet opens to allow fluid in the metering chamber to flow to the patient. Then, the outlet closes, and the process repeats itself. The controller, by determining the frequency with which the sequence of events occurs, provides an upper limit to the amount of fluid which can pass to the patient.

The section of resilient membrane also plays a role in the valving of the inlet and the outlet of the casette. Liquid passes through a dimple formed in the polyurethene section located over a flat valve face formed in the rigid plastic.

The controller has, for the inlet and outlet valves, separate rods having their ends formed in the shape of a sharp edge. To close the particular valve, the controller moves the rod towards the flat valve face in the rigid plastic. As the rod moves in this direction, its knife contacts the center of the dimple in the resilient plastic and collapses it against the flat face of the rigid plastic. When the rod has securely placed the resilient plastic against the flat face, no fluid can flow past the valve.

To fully control the casette, the controller need only move the rods provided for the inlet and the outlet valves. Consequently, it possesses far less weight than the peristaltic pumping type of equipment. Thus, it may simply attach to a casette located in the flow line connecting the intravenous solution to the patient. Its light weight allows the tubing itself to provide its total support. It needs no auxiliary shelf or surface.

Moreover, the total motion produced by the controller simply consists of moving the valving rods twice during each cycle of operation. In comparison to the peristaltic pump, moving these rods the minimal distance required to open and close the valves consumes very little electrical energy. Consequently, the controller portends the likelihood of operating upon battery, as opposed to line, current.

However, Turner et al's apparatus displays characteristics that could, in severe circumstances, limit its reliability in continued use. The polyurethane dimples forming part of the valves can suffer a permanent alteration in their configuration after experiencing the continued attack of the valving rods from the controller. Upon the retraction of the rods into the controller to open the valve, the dimple may not resume its former shape; it would thus keep the valve in a closed configuration.

Moreover, the same permanent shape distortion can occur to the resilient polyurethene forming part of the metering chamber. It may simply fail to revert to the configuration that provided the metering chamber with its measured volume. When in the volumeless configuration, no fluid can flow through the casette to reach the patient, regardless of the action of the controller.

Furthermore, the resilient polyurethene needs the hydrostatic head operating against the closed outlet valve to flex to its configuration in which the metering chamber has volume. Outside of the controller, the polyurethene will assume a configuration that will prevent the flow of fluid to the patient. In the case of an inoperative controller then, the casette totally prevents the passage of intravenous fluid to the intended recipient.

SUMMARY

Utilizing a casette with a stretchable elastomeric membrane obviates many of the problems produced by the resilient polyurethene utilized by Turner et al. Moreover, the elastomeric membrane also produces additional benefits for the casette and the controller.

A fluid measuring device including the membrane should include a fluid-tight metering chamber formed, at least in part, from the membrane. Moreover, it should have an opening in fluid communication with the chamber's interior. The opening, of course, allows for the ingress and egress of the fluid into and out of the chamber.

As the fluid enters, the shape of the membrane forming part of the chamber changes. Typically, the membrane stretches to accommodate the additional fluid or liquid.

The membrane could increase in size until it reaches its limit of expansion. At that point, however, it becomes susceptible to bursting. Moreover, different sections of membrane formed from the same elastomeric material can display different maximum expansions. Consequently, metering chambers utilizing sections of membrane having the same size could possess different volumes.

However, the membranes must not be allowed to reach a size where they could burst and they must all provide the same uniform maximum volume for the metering chamber. Consequently, the fluid measuring device should include a chamber-defining means. This component limits the stretching of the membrane forming part of the chamber to a size larger than its least stretched size that it can have as part of the chamber.

Typically, the fluid measuring device, or casette, possesses two sections of rigid material, generally plastic. The two sections remain rigidly affixed to each other with the elastomeric membrane held between them. One of the sections of the plastic and the membrane form the metering chamber. The other piece of plastic performs the role of the chamber-defining means. It provides a surface against which the membrane makes contact as it expands when sufficient fluid has entered the chamber.

When the membrane has fully contacted the second piece of plastic, it can expand no further. At this point, the chamber can accept no further fluid. Thus, the second piece of plastic provides the chamber with a definite and well known volume.

The second plastic section may also serve further functions. First, by limiting the membrane's expansion, it keeps it to a size at which no substantial likelihood of bursting appears.

Second, the second plastic piece may squeeze the periphery of the elastomeric membrane against the first plastic piece which forms part of the metering chamber. A seal between the chamber's membrane and plastic piece thus results to make the chamber fluid tight except at the provided openings. This represents a particularly important role because of the different natures of the materials constituting the two portions of the metering chamber.

Typically, the casette has two openings. The first, a closable inlet means, allows fluid to flow into the metering chamber. The second, a closable outlet means, similarly permits the flow of the fluid out of the metering chamber. The provision of these two openings results in a unidirectional flow of the fluid through the casette.

To provide the required control over the casette, as with the Turner et al. apparatus above, the controller must, with the outlet closed, open and close the inlet. This allows the intravenous solution to flow into the metering chamber. After the closing of the inlet, the controller must then open the outlet to allow this fluid to flow to the patient. The outlet next closes to prepare the metering chamber for the next dose of liquid.

In addition to the membrane section which forms part of the metering chamber, further sections may also form part of the inlet and the outlet. Typically, all sections of the membrane will simply represent different parts of the same piece of material. When the controller closes the inlet, the appropriate portion of the membrane would change its shape to seal off the inlet. This prevents the flow of fluid through it into the metering chamber. Similarly, the membrane located in the region of the outlet, when the controller closes it, changes its dimension. This seals it to the outlet and prevents the flow of fluid through it out of the chamber. In either instance, the membrane, under the action of the controller, contacts the first piece of rigid plastic to close off the appropriate channel.

The casette's elastomeric membrane provides it with a number of benefits. The elastomeric material constituting the membrane does not possess a definite configuration. Accordingly, changing its shape through use does not result in an acquisition of a new and undesired configuration. Thus, the portion of the membrane forming the metering chamber can expand and contract without "flexing" into a set shape that prevents its further use. Similarly, the sections of the membrane used as part of the inlet and outlet openings can not become set into a closed configuration due to the controller's repeated valving of the casette.

Furthermore, the elastomeric nature of the membrane offers very little resistance to the activities in which it takes part. Thus, a minimal hydrostatic head from the solution entering the casette suffices to expand the membrane forming part of the metering chamber. This ease of introducing the fluid into the casette obviates any need for an upstream drip chamber or standpipe. Thus, it may connect directly to the I.V. bottle which accordingly increases its vertical range of operation.

Additionally, the resiliency of the membrane allows it to readily contract upon the opening of the outlet to let fluid flow out of the casette. In fact, the membrane's tendency to contract when stretched, actually helps force the fluid to flow through the outlet to the patient.

Moreover, the membrane simply contracts as the fluid passes through the outlet. The volume of the metering chamber simply disappears during this operation. Consequently, the casette does not require any further aid in emptying the chamber, such as the arcuate slots seen in Turner et al's apparatus.

Moreover, the elastomeric nature of the membrane allows it to act as the hermetic seal between itself and the section of plastic forming part of the metering chamber. This obviates the problem of an imperfect adherance between the two components. The two plastic pieces merely squeezing the edge of the membrane between them provides a secure seal against the unintended escape of fluid.

The use of an elastomeric material does, however, present a problem in the construction of a casette. The surface of the elastomeric material possesses a tacky texture. This could cause it to adhere to the instruments assisting in the construction of the casette. Moreover, it could stick to the plastic pieces of the casette while in use. However, exposing the membrane to a mild solution of sodium hypochlorite and hydrochloric acid reduces that tackiness while not affecting the other properties of the membrane.

Further, the production of the actual sections of membrane used for the casette represents a very simple and time-saving task. The elastomeric material, such as silicone or natural rubber, generally comes in large sheets. After the treatment to remove the surface tackiness, an appropriate sharp instrument may simply cut appropriately shaped sections of the membrane. The sections may then immediately find use in the construction of a casette. The membrane does not require molding to a particular configuration as does the resilient polyurethene diaphram used previously.

DETAILED DESCRIPTION

Figure 1:
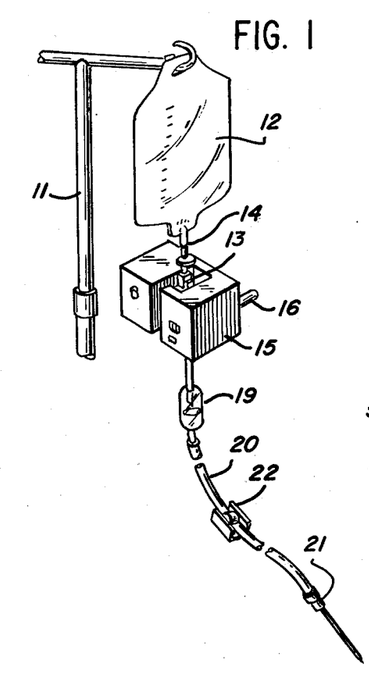
FIG. 1 shows intravenous equipment including all the components used for administering an I.V. solution to a patient, including a casette and a controller for limiting the flow rate.

A set of components for administering an intravenous solution to a patient appears in FIG. 1. The stand 11 holds the bottle 12 of intravenous solution at a sufficient height above the patient to allow for a gravity flow of liquid with sufficient pressure. The stand 11 either attaches to the bed or a wheelchair or simply sits upon the floor.

The container 12 may either take the form of either a glass or a plastic bottle. The latter represents the more modern version and possesses many well-known advantages aside from its use with the casette and controller discussed below.

The casette 13 connects directly to the bottle 12. Its pointed hollow spike 14 enters the interior of the bottle 12 and provides a flow path for the liquid to the casette 13.

The controller 15 attaches to the casette 13 to limit the flow of the intravenous solution to the patient. The knob 16 on the back of the controller 15 allows for its secure attachment to the casette 13 and its subsequent disengagement after use.

The controller 15 operates on a battery and has minimal weight. Consequently, both it and the casette 13 may simply remian suspended from the intravenous bottle 12. Their minimal mass gives assurance that the components cannot separate except with the significant assistance of an attendant.

The fluid that the controller 15 allows to pass through the casette 13 then enters the usual drip chamber 19. From there, it passes through the tubing 20 and the hypodermic needle 21 to the patient. The usual clamping device 22 may accompany the tubing 20 to assist the attendant when beginning or ending the administration of the fluid to the patient.

Figure 2:
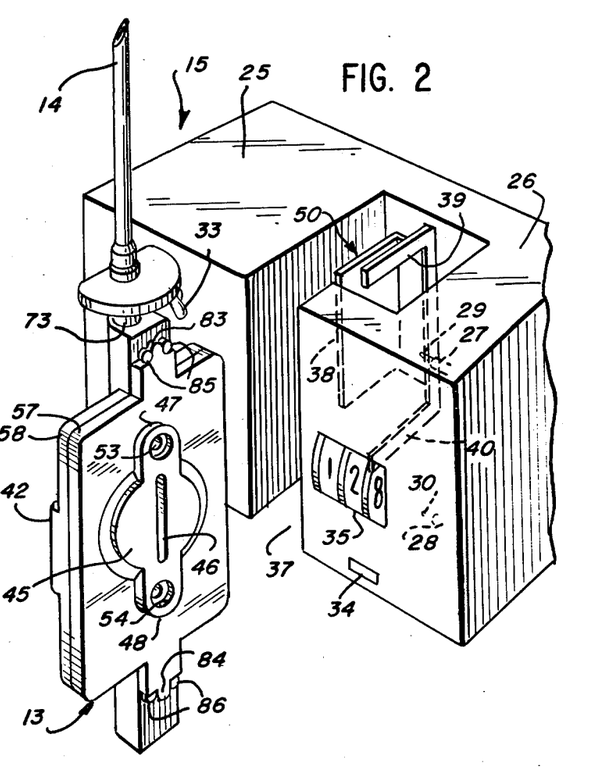
FIG. 2 depicts the external features of a casette and controller.

The controller, shown generally at 15 in FIG. 2, includes the first half 25 which may house the usual electronic components. The second half 26 may then include an electromagnet which functions to open and close the casette's inlet and outlet. Also in the figure, the alignment bosses 27 and 28 and the valving rods 29 and 30 appear in phantom toward the right. On the face of the controller 15 appear the on-off switch 33, the light 34, and the rotating selector switch 35 for choosing the desired flow rate.

Between the two halves 25 and 26 appears the slot 37 into which the casette 13 may enter. As the casette 13 enters into the opening 37, it wedges between the flat plate 38 on one side and the two arms 39 and 40 on the other. The distance between the plane of the plate 38 and the plane of the arms 39 and 40 barely accommodates the width of the casette 13. This snug fit helps orient the casette 13 relative to the valving members 29 and 30.

To provide firm contact with the plate 38, the casette includes the ridges 42 (also seen in phantom in FIG. 5) on its longer edges to assure a secure contact with the plate 38. The casette 13 requires the ridges 42 since a channel passing between the inlet and the outlet creates a ridge of a similar passing down the middle of the casette on the side not seen in FIG. 2.

Controller 15 may function in the manner described in the copending U.S. application of Nick Zissimopoulous, Ser. No. 878,970, filed Feb. 17, 1978. Alternatively, controller 15 may comprise a valving system as disclosed in U.S. Pat. No. 4,121,584.

On the side visible in FIG. 2, the casette 13 includes the flat surface 44. In the middle of the flat surface 44 appears the projection 45 which extends outward from it. The projection 45 first provides room for the flexible elastomeric membrane to expand inside of the casette 13. The slot 46 in the projection 45 allows for the equalization of air pressure as the membrane expands and contracts.

The projection 45 also assists in the alignment of the casette 13 in the holder 15. As the casette 13 enters the opening 37, the arms 39 and 40 barely have a sufficient distance between them to lie above and below, respectively, the projection 45. In other words, the bottom of the arm 39 contacts the upper most point 47 of the projection 45. Similarly, the top of the bottom arm 40 contacts the point 48 lying at the bottom of the projection 45. The tight fit of the projection 45 between the arms 39 and 40 aligns the casette 13 vertically within the controller 15.

Once inserted between the plate 38 and the arms 39 and 40, the knob 16 of FIG. 1 moves the entire metal section 50, which includes these components, to the right, as viewed in FIG. 2. As it does, the bushings 27 and 28 and the movable valve members 29 and 30 enter the openings 53 and 54, respectively, in the protuberance 45. The bushings 27 and 28 fit snugly inside of the openings 53 and 54. This tight fit assures the proper alignment of the movable valving members 29 and 30 relative to the valve seats in the casette which receive discussion below.

To open and close the inlet and outlet, the valve members 29 and 30 extend through the large openings 53 and 54. They then enter the smaller openings further inside and actually make contact with the elastomeric membrane contained in the casette.

Specifically, the casette 13 includes the two sections of rigid plastic 57 and 58 securely fused together. The elastomeric membrane, which appears in FIG. 3, sits between them to provide part of the metering chamber, the inlet, and the outlet. The surfaces of the two plastic sections 57 and 58 which face each other appear in FIGS. 4 and 5, respectively. The section of stretchable elastomeric membrane 60, when in the casette 13, adjoins the two surfaces shown in these figures.

The cover section 57 of plastic includes the flat surface 44 and the projection 45. It constitutes the piece of plastic forming the right-hand portion of the casette 13 as seen in FIG. 2. The surface 61 of the cover section 57 appears in FIG. 4, but not FIG. 2; it faces the inside of the casette and contacts the base section of plastic 58.

Figure 4:
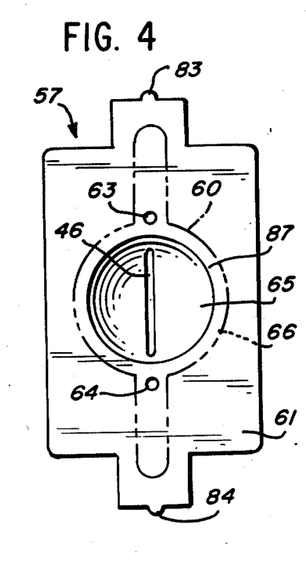
FIG. 4 illustrates the piece of rigid plastic which serves to define the size of the metering chamber in the casette.

As the controller 15 moves the valving members 29 and 30 into a position to close the inlet or the outlet, respectively, they move entirely through the cover section of plastic 57. FIG. 4 shows the openings 63 and 64 in the plastic section 57 through which these members move to contact the membrane 60, shown in phantom in FIG. 4 in its proper orientation. When the valving members 29 and 30 project the maximum distance through the opening 63 and 64, they stretch the neighboring portion of the membrane 60 until it contacts the base plastic section 58 and closes, respectively, the inlet and the outlet. When the casette 15 retracts them, the elastomeric membrane 60 contracts and allows the passage of fluid into or out of the casette 13, as appropriate. Specifically, the retraction of the valving member 29 from the opening 63 by the controller 15 allows fluid to flow into the metering chamber. Retracting the member 30 in the opening 64 allows fluid from the metering chamber to flow to the patient.

Figure 3:
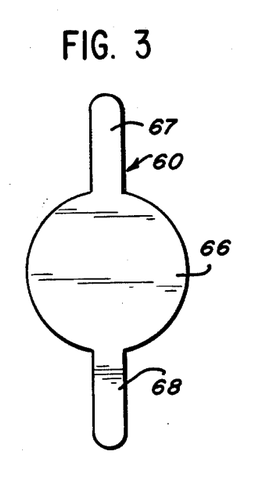
FIG. 3 shows a section of elastomeric membrane used in the casette of FIG. 2.

At its middle, the cover section of plastic 57 has the concave depression 65. In fact, the projection 45, seen on the other side of the cover section 57 in FIG. 2, accommodates the depression 65. In FIG. 3, the membrane 60 has the circular section 66 which fits over the depression 65.

When fluid enters the casette 13, the circular part 66 expands until it contacts the plastic forming the depression 65. At that point, it can expand no further to allow additional fluid to enter the casette. Consequently, the shape of the depression 65, rather than any characteristic of the elastomeric membrane 60, determines the volume of fluid that the casette 13 provides in each cycle of its operation. The slot 46, again seen in FIG. 4, allows for the escape of air as the entering fluid causes the membrane's circular section 66 to expand into the depression 65.

As seen in FIG. 3, the section of membrane 60 has the two legs 67 and 68 adjacent to its circular central portion 65. The purpose of the legs 67 and 68 becomes apparent from a discussion of the base section of plastic 58, which appears in FIG. 5. As seen there, the opening 71 allows for the entrance of fluid into the channel 72, which represents a groove into the base section 58. In order to arrive at the opening 71, the fluid from the bottle 12 flows into the pointed rigid tubular section 14, seen in FIG. 2, and into the inlet channel 73 at the top of the casette 13. The groove channel 72 provides a conduit for the fluid from the port 71.

Figure 5:
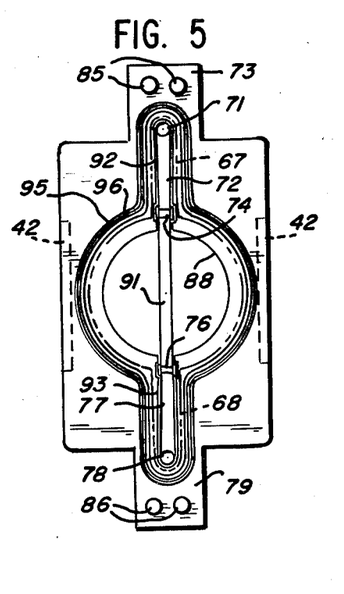
FIG. 5 shows the section of rigid plastic which forms part of the metering chamber and also the inlet and outlet leading to it.

The fluid flowing in the groove 72 passes to the flat shallow region 74. The flat surface 74 functions as the face for the valve member 29 to close the inlet and prevent the flow of fluid into the metering chamber of which the flat circular surface 75 forms part. When the movable member 29 does not contact the flat valve face 74, the fluid passes to the metering chamber until the latter becomes full.

Specifically, the metering chamber includes the large flat circle 75 in the base section of plastic 58. The flat circle 75 makes actual contact with the fluid. The circular section 65 of the membrane 60 forms the remainder of the metering chamber. When the metering chamber empties, however, the circular section 65 of the elastomeric membrane 60 actually contacts the flat circle 75 in the base piece of plastic 58. When the metering chamber fills, the concave depression 65 in the cover plastic slip 57 limits the expansion of the membrane 60. This provides this metering chamber with a maximum predetermined measured volume.

To depart the metering chamber, the fluid then flows past the shallow flat outlet valve face 76. From there, it travels along the groove 77 formed into the base section of plastic 58 until it reaches the outlet port 78. From there, it flows through outlet channel 79 and then into the usual drip chamber 19 seen in FIG. 1.

The valve members 29 and 30 must force the membrane 60 into contact with the inlet valve face 74 and the outlet valve face 76 in order to close the casette's inlet and the outlet, respectively. To do so, the movable members 29 and 30 pass through the cover slip of plastic 57. As mentioned above, the openings 63 and 64 in the plastic cover section 57 permit the movable members 29 and 30 access to the membrane 60 in the immediate vicinity of the valve faces 74 and 76. Consequently, for the valve members 29 and 30 to function properly, the openings 63 and 64 must occupy a position immediately over the valve faces 74 and 76. This, in turn, requires a proper orientation of the cover slip 57 to the base section of plastic 58. To provide this orientation, the cover slip 57 includes the knobs 83 and 84 at either end. When the two plastic sections 57 and 58 fit together, the knob 83 sits between the two protuberances 85 provided at the top of the base section of plastic 58. Similarly, the knob 84 will barely fit between the two knobs 86 at the bottom of the base section 58. The close fit of the knobs 83 and 84 between the protuberances 85 and 86, respectively, assures the proper alignment of the openings 63 and 64 over the valve faces 74 and 76.

The correct orientation between the plastic sections 57 and 58 also achieves a proper hermetic seal between the elastomeric membrane 60 and the base plastic section 58. To provide the seal, the cover section of plastic 57 has the completely flat surface 61 except for the concave depression 65. The outer circumference 87 of the concave depression 65 has a slightly smaller diameter than the circumference 88 of the raised circular portion 75 of the base plastic section 58. When the plastic sections 57 and 58 properly fit together, the circumference 87 falls inside of the larger circumference 88.

As seen in FIGS. 4 and 5, the membrane 60 covers both of the circumferences 87 and 88. Consequently, when affixed to each other, the flat surface 61 squeezes a small angular ring of the membrane 60 against the elevated circular portion 75. The width of the small ring of squeezed membrane 60 equals the distance between the smaller circumference 87 on the cover slip 57 and the larger circumference 88 on the base section 58. The concave region 65 within the circumference 87 then allows for the expansion and contraction of the membrane 60 to provide the metering chamber.

The raised circle 75, however, has the channel 91 passing down its center. As discussed further below, the channel 91 allows the flow of fluid from the inlet port 71 to the outlet port 78 when the casette 13 does not sit inside of the controller 15. However, at the two locations where the groove 91 meets the circumference 88, no seal of the membrane 60 to the base plastic section 58 occurs. The lack of a seal at these points, of course, allows fluid to flow from the inlet port 71 into the metering chamber and out through the outlet port 78.

However, fluid must not escape between the inlet port 71 and the circular region 75 or between the circular region 75 and the outlet port 78; the edges of legs 67 and 68 of the membrane 60 must provide a hermetic seal around the channels 72 and 77. To provide this seal, the casette's base section 58 includes the elevated ridge 92 which passes from the circumference 88, around one side of the inlet valve face 74, down to and around the inlet port 71, back to the other side to the valve face 74, returning to the circumference 88. Similarily, the ridge 93 passes from the circumference 88, around the outlet valve face 76 on one side, down to and around the outlet port 78, back to and around the outlet valve face 76, and to the circumference 88. The ridges 92 and 93 have the same height as the elevated circular region 75 to which they connect.

As indicated in the figure, the legs 67 and 68 of the membrane 60, surround, respectively, the ridges 92 and 93. The flat surface 61 of the cover slip 57 squeezes the legs 67 and 68 against the ridges 92 and 93 to provide a hermetic seal around them. Thus, the total hermetic seal of the membrane 60 to the base section of plastic 58 passes along the ridge 92, for example, around one half of the circumference 88, along the bottom ridge 93, and back along the other half of the circumference 88 to the inlet ridge 92. This closed seal prevents any fluid from escaping from between the membrane 60 and the base plastic section 58. All the fluid that enters through the inlet port 71 can only exit through the outlet port 78.

A weak battery could cause the controller 15 to cease functioning. That would warrant its removal from the casette 13. Additionally, a controller may not be available when required. In either event, the casette 13 would not have a valve member to close its outlet port 78. As a result, any fluid in the casette would flow out through the outlet 78. Under these circumstances the central circular region 65 of the membrane 60 would most likely lie against the flat surface 75 of the base plastic section 58. Fluid entering at the inlet port 71 could possibly not force the circular membrane section 65 to move from the flat circle 75 and, thus, not flow to the outlet port 78.

The channel 91, formed into the flat circular region 75 prevents the casette from blocking all flow of fluid from the bottle 12. It assures a path for the fluid from the port 71 to the outlet port 78 even in the absence of a controller. Although the membrane may lie directly on top of the flat surface 75, the groove 91 beneath the membrane will permit the passage of fluid as desired. In that instance, the clamping device 22 of FIG. 1 or some other flow-controlling device would have to limit the amount of fluid received by the patient. Thus, the groove 91 assures that the casette 13, when included as part of the intravenous apparatus, does not totally block the flow of solution to the patient.

The groove 91, however, does not affect the volume of the metering chamber formed between the flat circular surface 75 and the circular portion 65 of the membrane 60. Because of capillary action, fluid within the groove does not drain upon the opening of the casette's outlet 78. Consequently during its normal operation, the casette 13 has the same predetermined maximum volume as though the groove 91 did not exist. That volume, of course, equals the space between the membrane 60 in its most expanded form inside of the depression 65 and the flat surface that would result if the circular surface 75 did not have the groove 91 in it.

As a further feature, the base section 58 includes the ridge 95 inside of which sets the elastomeric membrane 60. The ridge 95 forms a closed loop and has a larger cross-sectional area than the ridges 92 and 93 that provide for the hermetic seal of the membrane 60. The ridge 95, furthermore, has a triangular cross-sectional area so that, at its top, it has a sharp edge 96 which also forms a closed loop. The ridge 95 functions in the fusion of the cover slip 57 to the base section 58 of plastic.

In providing the final casette, the membrane 60 lies on top of the base section of plastic 58. The cover slip 57, properly aligned, sits over the section with the knobs 83 and 84 between the protuberances 85 and 86, respectively. Applying ultrasonics to the components causes the ridge 95 to melt and fuse to the cover slip 57. Thus, it provides a weld between the two sections 57 and 58. The triangular shape of the ridge 95 with the sharp edge 96 causes it to preferentially capture the ultrasonic energy and melt before the other portions of the plastic pieces 57 and 58. For this purpose, the plastic constituting the sections 57 and 58 should have a thermoplastic nature. An impact-modified acrylic resin with a rubber filler, such as that sold under the trademark Plexiglas-DR ® by the Rohm & Haas Co. represents a suitable choice.

The membrane 60 should have sufficient stretchability and longevity to last the usual 24 hours that a particular intravenous set can service the patient. After the passage of that time, a new set replaces the used one. Furthermore, the membrane 60 should, of course, not introduce toxic chemicals into the intravenous solution. A latex membrane performs the functions admirably. The sheets of latex entitled "Dental Dam" manufactured by the Hygenic Dental Manufacturing Co. represents a suitable choice. Centrifuging it at least twice eliminates any chemicals that it might possess.

The latex material, however, has a tacky surface. This could cause it to adhere, in use, to either the depression 65 or the flat circular surface 75. Moreover, it vastly increases the difficulty of initially producing the casette. A brief treatment with a mild sodium hypochorite solution will serve to reduce the superficial tackiness without otherwise affecting the properties of the membrane. Specifically, the solution should include 1.5 parts by weight of 5.25% sodium hypochorite in water; 0.5 parts of 37% industrial grade hydrochoric acid; and 98 parts of water. The membrane should then remain immersed in this solution for a period of 15 seconds.

When the controller's metal section 50, of FIG. 2, has firmly engaged the casette 13, the bushings 27 and 28 fit into the openings 53 and 54 of the cover plastic section 57. This places the valve members 29 and 30 in alignment with the small openings 63 and 64 through which they move to contact the membrane 60. Ideally, the valving members 29 and 30 attach to a bistable device which will cause at least one to occupy its protracted position in which it closes its valve. This bistable operation of the valving members 29 and 30 thus assures that at least one valve on the casette 13, while in the controller 15, will close. This will occur regardless of the nonfunctioning of the controller due to such causes as a weak battery. Consequently, as long as the casette 13 remains in the controller 15, no uncontrolled amounts of fluid can pass to the patient.

Moreover, the controller 15, as it opens one valve and closes the other, accomplishes the latter task first. In other words, it closes the open valve before it allows the closed valve to open. By closing the one valve before opening the other, the controller maintains strict control over the flow of fluid through the casette 13. Otherwise, an unknown quantity of fluid could flow directly through the casette during the time that both valves remained open if the controller did not function thusly.

Figure 6:
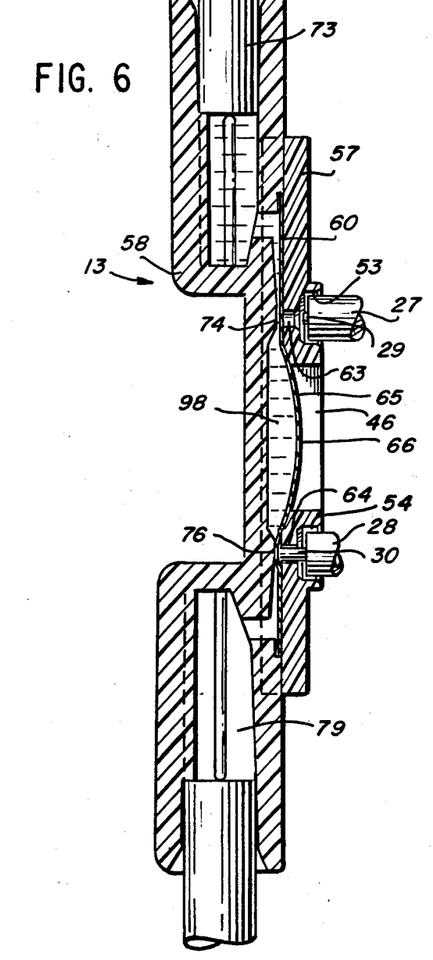
FIG. 6 gives a cross-sectional view of a casette formed from the components of FIGS. 3, 4, and 5 in a configuration in which the inlet has opened and allowed the metering chamber to fill.

Using the preferred procedure given above, the delivery of a specified volume of fluid by the casette 13 and the controller 15 begins with the closing of the outlet valve and the opening of the inlet valve. This requires the protraction of the outlet valve 30 and the retraction of the inlet valve member 29, as shown in FIG. 6. In this configuration, fluid from the inlet channel 73 may enter the metering chamber 98 between the flat surface 75 of the base section of plastic 58 and the circular region 66 of the membrane 60. The membrane's circular section 66 then expands to accommodate the fluid until it contacts the concave depression 66 in the cover slip 57. At that point, no further fluid can enter the casette 13 even if the inlet valve member 29 allows the inlet 71 to remain open for an additional period of time. The metering chamber 98 has accordingly filled with fluid.

Figure 7:
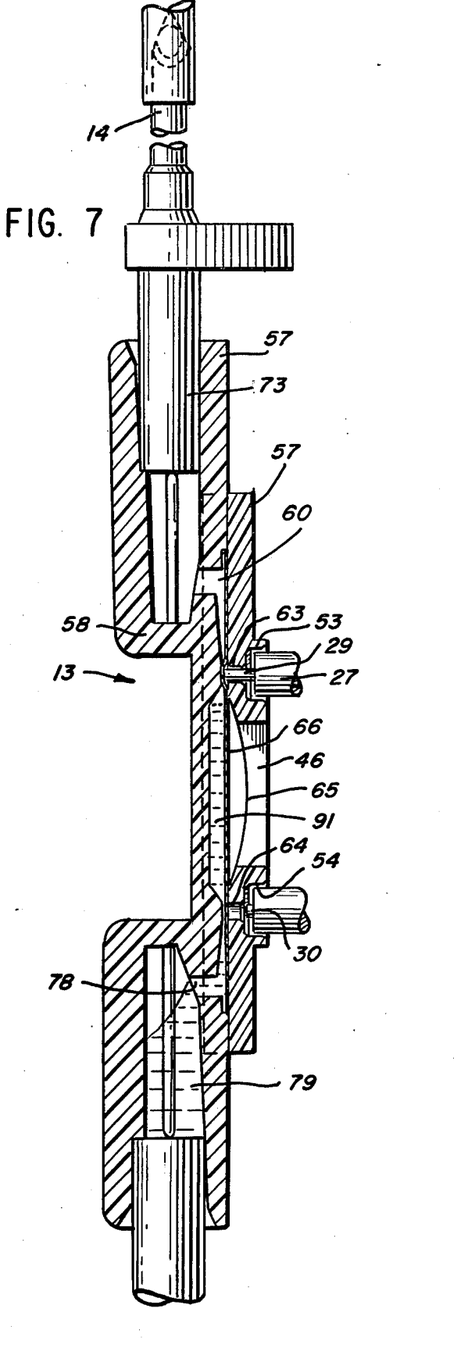
FIG. 7 has the same casette as FIG. 6 but in a configuration in which the outlet has opened to allow fluid from the metering chamber to pass to the patient.

With the metering chamber 98 full, the controller 15 then extends the inlet valve member 28 to close the inlet and subsequently retracts the outlet valve member 30 to open the outlet as seen in FIG. 7. The fluid in the metering chamber 98 may then flow through the channel 79 out the outlet port 78 and down the outlet channel 79 to the patient. The total amount of fluid that may flow during one such cycle of operation, of course, equals the volume of the metering chamber 98. The amount of fluid received by the patient over a period of time results from the number of cycles of operation of the controller during that time.

Also in FIG. 7, the groove 91 retains fluid even with the outlet valve member 30 retracted and the membrane 66 in its least stretched configuration. Accordingly, this fluid does not contribute to the volume that the metering chamber 98 can deliver during a single cycle of operation. The groove 91, however, will provide a conduit from the inlet channel 73 to the outlet channel 79 when neither the inlet valve member 29 nor the outlet valve member 30 engages the membrane 60.

An alternate casette 101 appears in FIGS. 8 through 12. It includes the base section of plastic 102 of FIG. 8, the cover plastic section 103 of FIG. 9 and the membrane 104 of FIG. 10. The casette formed from these components experiences a more facile production and displays greater reliability in service.

Figure 8:
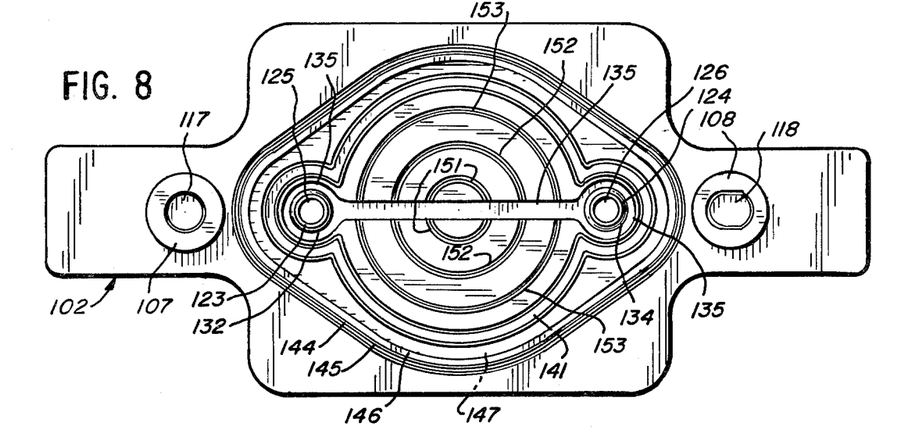
FIGS. 8, 9, and 10, show the base plastic part, the cover slip, and the elastomeric membrane, respectively, of an alternate form of casette.
Figure 9:
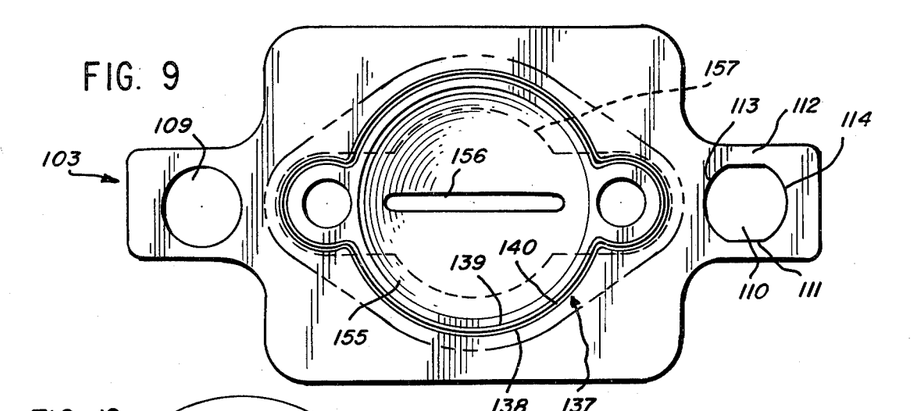
Figure 10:
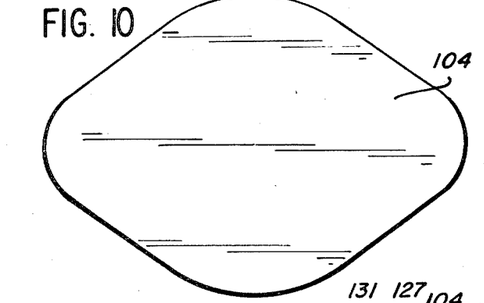

The base plastic section 102 includes the circular projections 107 and 108 near its ends. These projections 107 and 108 fit into the openings 109 and 110 in the cover slip 103 to properly orient the two sections when making the casette. The opening 109 has a circular outline so that it snugly fits around the circular projection 107.

The other opening 110, however, has a somewhat oblong appearance. Its shape allows a snug fitting of the projection 108 between its sides 111 and 112. However, the circular projection 108 has a freedom of longitudal motion between the ends 113 and 114 of the opening 110.

Nonetheless, the freedom of motion of the projection 108 in the opening 110 does not allow any latitude in the orientation of the two sections 102 and 103 relative to each other in the final casette. The snug fit of the circular projection 107 in the circular opening 109 prevents relative motion between the two sections 102 and 103 in the longitudal direction that the projection 108 can move in the oblong opening 110. The additional size of the opening 110 between its ends 113 and 114 simply allows greater manufacturing tolerance between the projection 108 and the opening 110. The close fit of the projection 107 in its opening 109 adequately compensates for the greater tolerance thus permitted to the manufacturing process.

Inside of the circular projection 107 appears the circular indentation 117. An oblong indentation 118 appears inside of the circular projection 108. The indentations 117 and 118 accommodate the circular alignment pins such as the projection 119 in FIG. 11. The member 119 attaches to the controller 15 and serves to orient the casette 101 relative to it.

Again, the oblong nature of the indention 118 would allow the circular projection that fits inside some freedom of motion in the direction towards the indentation 117. However, the snug fit of the member 119 inside of the indentation 117 prevents any motion of the casette 101 in the direction that a circular member could move while inside the indentation 118. Providing the oblong shape to the indentation 118 minimizes the manufacturing controls required in producing the casette while sacrificing absolutely no performance in the final product. important facet of the alignment indentations 117 and 118. The alignment openings 53 and 54 appear in the cover slip 57 of the casette 13. However, the valve members 29 and 30 must have proper alignment relative to the valve faces 74 and 76. Thus, any misalignment between the cover plastic section 57 and the base plastic section 58 must result in a misalignment between the valve members 29 and 30 and their respective valve faces 74 and 76. This would occur even though the bushings 27 and 28 properly fit within their respective openings 53 and 54.

Figure 11:
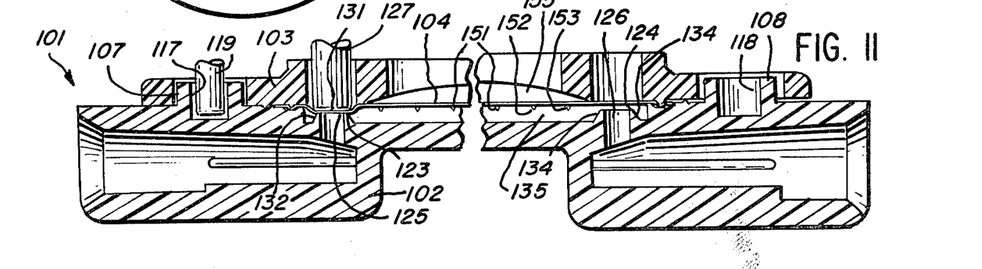
FIG. 11 gives a cross-sectional view of a casette formed from the components of FIGS. 8, 9, and 10 with the right half showing the two pieces of plastic before fusing together and the left half showing them afterwards.

In distinction, FIG. 11 shows that the alignment indentations 117 and 118 appear in the base section of plastic 102 rather than the cover slip 103. The valve faces 123 and 124 also appear on the base plastic section 102. Thus, the alignment indentations 117 and 118 appear on the same piece of plastic as do the valve faces 123 and 124. Consequently, the alignment between the valve faces 123 and 124 and the casette 101 does not depend upon the alignment between the two pieces of plastic 102 and 103. The indentations 117 and 118 in the base piece of plastic 102 provide for the direct alignment of the valve faces 123 and 124 relative to the controller.

As seen in FIGS. 5 and 6, the inlet valve face 74 consists simply of a flat surface in the channel 72. To close the inlet, the valve member 29 must do more than simply seat upon the face 74. It must cause the membrane 60 to contact the valve face 74 across the entire width of the channel 72 and to also firmly meet the sides of the channel 72. This seal along three surfaces requires structures manufactured to a high degree of accuracy.

The casette 101 in FIG. 11 requires no such degree of exactness for its valves. The valve seats 123 and 124 actually surround the inlet port 125 and the outlet port 126, respectively. To close the inlet, the valve member 127 need only cause the membrane 130 to contact the flat valve surface 123 in a closed circle surrounding the inlet port 125. The valve member 127 does not have to cause the membrane to contact anything other than the single flat surface 123. In particular, it does not have to make firm contact with another surface lying perpendicular to the flat valve face 123. Accordingly, the member 127 need only have a flat bottom surface 131 larger than the inlet port 125. This will cause the membrane 130 to seal against the flat valve face 123.

Additionally, the flat surface 123 adjoins the sloping surface 132 while the outlet face 124 adjoins the sloping surface 134. These surfaces 132 and 134 elevate the flat surfaces 123 and 124 above the channel 135 which surrounds them and, accordingly, facilitates the meeting of the membrane to the valve surfaces 123 and 124.

The cover slip 103, seen more clearly in FIG. 9, includes the ridge 137 formed from the two sides 138 and 139 which meet at the pointed edge 140. The edge 140 of the ridge 137 finds use during the manufacturing of the casette 101. Upon the completion of the casette's manufacture, the ridge 137 has no further function.

Figure 12:
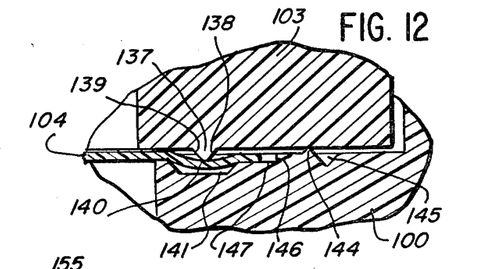
FIG. 12 gives an enlarged view of the two pieces of plastic of the right half of FIG. 11 prior to bonding in the region of the hermetic seal formed between the elastomeric membrane and the section of plastic on the bottom.

Prior to fusion, the cover slip 103 and the base section 103, when opposed with the membrane 104 between them, have the appearance given in the right side of FIG. 11. FIG. 12 magnifies the view in the region of the ridge 137. As shown there, the ridge's edge 140 makes contact with the membrane 104. During the fusion process, the two sections 102 and 103 receive ultrasonic energy. The vibrations induced in these two sections of material could cause the membrane 104 to move relative to either or both of the sections. The sharp edge 140 contacts the membrane 104 and keeps it in place during the ultrasonic fusion process. The base section of plastic 102 has the shallow channel 141 to accommodate the membrane 104 depressed by the edge 140.

The base section 102 also includes the ridge 144. During the fusion process of the two sections 102 and 103 to each other, the ridge 144 collects the ultrasonic energy, melts, and binds the two sections together. When it melts, the ridge 144 can produce more plastic than may fit between the two sections 102 and 103 when pressed together. Accordingly, the base plastic section 102 includes the groove 145 to accept any such additional plastic produced by the melting of the ridge 144.

Further, the base plastic section 102 has the short vertical surface 146 which provides the flat surface 147 upon which sits the membrane 104. The slight depression of the surface 147 allows sufficient space between the two sections 102 and 103 to accommodate the width of the membrane 104.

FIG. 8 also shows the semicircular grooves 151, 152, and 153 cut into the base section of plastic 102. These grooves all terminate at the channel 135. While priming the casette 101 at the beginning of actual intravenous use, any small air bubbles between the membrane 104 and the base casette section 102 can travel along the grooves 151, 152, and 153 to the center channel 135. The channel 135 then carries them to the outlet port 126 and to the usual drip chamber. The channel 135 also serves to assure a conduit between the inlet port 125 and the outlet port 126 when the casette 101 sits outside of a controller. In this regard it serves the same function as the channel 91 of the base section 58 shown in FIG. 5.

The cover section of plastic 103 in FIG. 9 includes a number of features similar to those of the cover section 57 in FIG. 4. Specifically, it has the circular concave depression 155 which allows the predetermined expansion of the membrane 104. This provides a metering chamber of known volume. Furthermore, the slot 156 allows for the equalization of the air pressure between the cover slip 103 and the membrane 104 as the latter expands and contracts.

The projection 157, shown in phantom in FIG. 9, appears on the other side of the cover slip 103 and accommodates the concave depression 155. It permits the orientation of the casette 101 between the arms 39 and 40 of the metal section 50 shown on the controller 15 of FIG. 2.

Accordingly, what is claimed is:

1. In a controlled volume administration set for liquids which defines a liquid flow path passing on one side of a flexible membrane positioned within a chamber-defining housing, and upstream and downstream valve apertures to permit valving members to alternatively and releasably block liquid flow through said flow path, said flexible membrane being elastomeric, the improvement comprising said flexible membrane normally occupying a flat configuration in said chamber defined by the housing, said membrane being sufficiently resilient to bulge outwardly to and against one side of the chamber when said chamber is filled on the opposite side of the membrane with liquid at a gravity pressure head typical of that found in parenteral solution administration, to permit said liquid to fill the chamber, and channel means defined in the wall of said chamber adjacent the liquid-receiving side of said membrane extending between the upstream and downstream valve apertures for maintaining an open passageway between said valve apertures regardless of the configuration of said membrane.

2. The controlled volume administration set of claim 1 in which said housing and flexible membrane contained therewith comprise a casette separable from said valving members.

3. The controlled volume administration set of claim 2 in which said membrane stretches to the maximum size permitted by said chamber under a hydrostatic head of at least two inches of water.

4. The controlled volume administration set of claim 3 in which said chamber-defining housing defines arcuate grooves in its chamber-defining wall leading to the flow path which passes through said downstream valve aperture.

5. The controlled volume administration set of claim 4 in which said casette defines a slot for the equalization of air pressure communicating through the wall thereof from the chamber on the side of said membrane which is opposed to the liquid-receiving side.

6. The controlled volume administration set of claim 5 in which said housing of the casette comprises a pair of housing parts which are held together about their periphery, with the periphery of said membrane squeezed together between said housing parts along their periphery to provide a fluid-tight seal.

7. The controlled volume administration set for liquids of claim 6 in which said membrane is sufficiently elastomeric, upon being in its outwardly bulging configuration with a chamber filled with liquid having a viscosity not substantially greater than that of water to contract again to its normal, flat configuration when said valving member permits fluid to pass through the downstream valve aperture.

8. The controlled volume administration set for liquids of claim 7 in which said casette is installed in a controller comprising said valving members, and adapted to retain the casette and pass said valving members through said upstream and downstream valve apertures to alternatively and releasably press against said membrane to block liquid flow.

9. The controlled volume administration set of claim 8 in which said membrane is made of natural rubber latex.

10. The controlled volume administration set of claim 9 in which said membrane exhibits reduced surface tackiness.

11. The controlled volume administration set for liquids of claim 1 in which said housing and flexible membrane contained therewith comprises a casette separable from the valving members, said casette comprising a pair of housing parts which are held together about their periphery, with the periphery of said membrane squeezed together between first portions of said housing parts to provide a fluid-tight seal, and second portions of said housing parts, spaced from said membrane and sealing said housing parts together, a first portion of said housing parts defining a slight depression relative to a second portion to allow sufficient space between the housing parts to accommodate the width of the membrane.

12. The controlled volume administration set of claim 11 in which one of said housing parts defines, adjacent the periphery of the membrane, an annular ridge, and the other of said housing parts defines an annular channel into which said ridge projects, said ridge pressing a peripheral portion of said membrane into said channel, said ridge and channel being positioned in said first portion.

13. The controlled volume administration set of claim 12 in which said chamber-defining housing defines arcuate grooves in its chamber-defining wall leading to the flow path which passes through said downstream valve aperture.

14. In a fluid-flow limiting device having metering means for holding a predetermined volume of a fluid; closable inlet means in fluid communication with said metering means for permitting the flow of a fluid into said metering means; closable outlet means in fluid communication with said metering means for permitting the flow of a fluid out of said metering means; and controlling means for sequentially: opening said inlet means, closing said inlet means, opening said outlet means, and closing said outlet means; a stretchable elastomeric membrane with a first portion of said membrane forming at least part of the metering means, a second portion of said membrane forming at least part of said inlet means, and a third portion of said membrane forming at least part of said outlet means; the improvement comprising said membrane being elastomeric and normally occupying a flat configuration, being sealed at its periphery within a chamber in a housing, one side of said membrane being in communication with the inlet and outlet means, said membrane being sufficiently resilient to bulge outwardly to and against one side of said chamber when said chamber is filled on said one side of the membrane with liquid at a gravity pressure head typical of that found in parenteral solution administration, and channel means for maintaining an open passageway from said inlet means to the outlet means regardless of the configuration of said membrane.

15. The fluid-flow limiting device of claim 14 in which said metering means, inlet means, and outlet means are defined by a generally rigid housing which carries said flexible membrane within said housing with the periphery of said membrane being in sealed relation to the housing, said housing and flexible membrane comprising a casette separable from the controlling means, said housing comprising a pair of housing parts which are held together about their periphery, with the periphery of said membrane squeezed together between first portions of said housing parts to provide a fluid-tight seal, and second portions of said housing parts, spaced from said membrane and sealing said housing parts together, a first portion of said housing parts defining a slight depression relative to a second portion to allow sufficient space between the housing parts to accommodate the width of the membrane.

16. The controlled volume administration set of claim 15 in which one of said housing parts defines, adjacent the periphery of the membrane, an annular ridge, and the other of said housing parts defines an annular channel into which said ridge projects, said ridge pressing a peripheral portion of said membrane into said channel, said ridge and channel being positioned in said first portion.

17. The fluid-flow limiting device of claim 16 in which said housing defines arcuate grooves in its chamber defining wall leading to the flow path which passes through said outlet means.

18. The fluid-flow limiting device of claim 15 in which said membrane is sufficiently elastomeric, upon being in its outwardly-bulging configuration with a chamber filled with liquid having a viscosity not substantially greater than that of water, to contract again to its normal, flat configuration when said valving member permits fluid to pass through the downstream valve aperture.

19. The fluid flow limiting device of claim 18 in which said casette is installed in a controller comprising valving members, and adapted to retain the casette and to pass said valving members through upstream and downstream valve apertures adjacent said inlet and outlet means, to alternatively and releasably press against said membrane to block liquid flow.

20. The fluid flow limiting device of claim 19 in which said membrane is made of natural rubber latex.

21. The fluid flow limiting device of claim 20 in which the membrane exhibits reduced surface tackiness.

22. The fluid flow limiting device of claim 21 in which said casette defines a slot for the equalization of air pressure communicating through the wall thereof from the chamber on the side of said membrane which is opposed to the liquid-receiving side.

23. The fluid flow limiting device of claim 22 in which said membrane stretches to the maximum size permitted by said chamber under a hydrostatic head of at least two inches of water.

* * * * *